(12) United States Patent
Bachinger-Colling et al.

(10) Patent No.: US 11,607,288 B2
(45) Date of Patent: Mar. 21, 2023

(54) SURGICAL TABLE, SURGICAL LIGHT, SYSTEM COMPRISING SURGICAL TABLE AND SURGICAL LIGHT, AND METHOD FOR OPERATING THE SYSTEM

(71) Applicant: TRUMPF MEDIZIN SYSTEME GMBH + CO. KG, Saalfeld (DE)

(72) Inventors: Timotheus Bachinger-Colling, Munich (DE); Andreas Huber, Munich (DE)

(73) Assignee: Trumpf Medizin Systeme GmbH + Co. KG, Saalfeld (DE)

(*) Notice: Subject to any disclaimer, the term of this patent is extended or adjusted under 35 U.S.C. 154(b) by 0 days.

(21) Appl. No.: 17/332,159

(22) Filed: May 27, 2021

(65) Prior Publication Data
US 2021/0369392 A1 Dec. 2, 2021

(30) Foreign Application Priority Data
May 29, 2020 (EP) .................................. 20177750

(51) Int. Cl.
*A61B 90/30* (2016.01)
*H05B 47/115* (2020.01)
(Continued)

(52) U.S. Cl.
CPC .............. *A61B 90/30* (2016.02); *A61G 13/02* (2013.01); *H05B 47/11* (2020.01); *H05B 47/115* (2020.01); *H05B 47/19* (2020.01)

(58) Field of Classification Search
CPC ....... A61B 90/30; A61B 90/35; H05B 47/115; H05B 47/11; H05B 47/19; H05B 47/10;
(Continued)

(56) References Cited

U.S. PATENT DOCUMENTS 6,591,239 B1 7/2003 McCall et al.
10,007,408 B2* 6/2018 Marka .................... A61B 34/25
(Continued)

FOREIGN PATENT DOCUMENTS

DE    102014212632 A1   12/2015

OTHER PUBLICATIONS

MedicaTradeFair "Medica 2009: LED—Operationsleuchte TruLight von TRUMPF Medizintechnik", Nov. 20, 2009, p. 1: URL:https://www.youtube.com/watch?v=tMq8Kq4rLCc [retrieved on Nov. 2, 2020.
(Continued)

*Primary Examiner* — Bao Q Truong
(74) *Attorney, Agent, or Firm* — Barnes & Thornburg LLP

(57) ABSTRACT

Provided are a surgical table comprising a surgical table controller configured to control at least one surgical table actuator of the surgical table, wherein the surgical table controller comprises an surgical table controller interface configured to be connectable to a controller of a further medical apparatus, a surgical light comprising a surgical light controller configured to control an intensity and to turn on and off at least one illuminant of the surgical light, wherein the surgical light controller comprises an surgical light controller interface configured to be connectable to a controller of a further medical apparatus, and a system comprising the surgical table and the surgical light, wherein the surgical table controller and the surgical light controller are configured to be connected to one another.

21 Claims, 1 Drawing Sheet

(51) Int. Cl.
*H05B 47/11* (2020.01)
*H05B 47/19* (2020.01)
*A61G 13/02* (2006.01)

(58) Field of Classification Search
CPC .... H05B 47/105; H05B 47/13; H05B 47/125; A61G 13/02; F21V 33/0068; F21V 33/0072
See application file for complete search history.

(56) References Cited

U.S. PATENT DOCUMENTS

| | | | |
|---|---|---|---|
| 2003/0195644 A1* | 10/2003 | Borders | A61G 12/00 340/568.1 |
| 2011/0037840 A1 | 2/2011 | Hiltl et al. | |
| 2015/0317068 A1 | 11/2015 | Marka et al. | |
| 2019/0249847 A1 | 8/2019 | Hallack et al. | |

OTHER PUBLICATIONS

KLSmartGroup "marLED XI Unsere neue Operationsleuchte", Apr. 11, 2019, p. 1: URL:https://www.youtube.com/watch?v=To6L8J0Oi1Q [retrieved on Nov. 2, 2020.

* cited by examiner

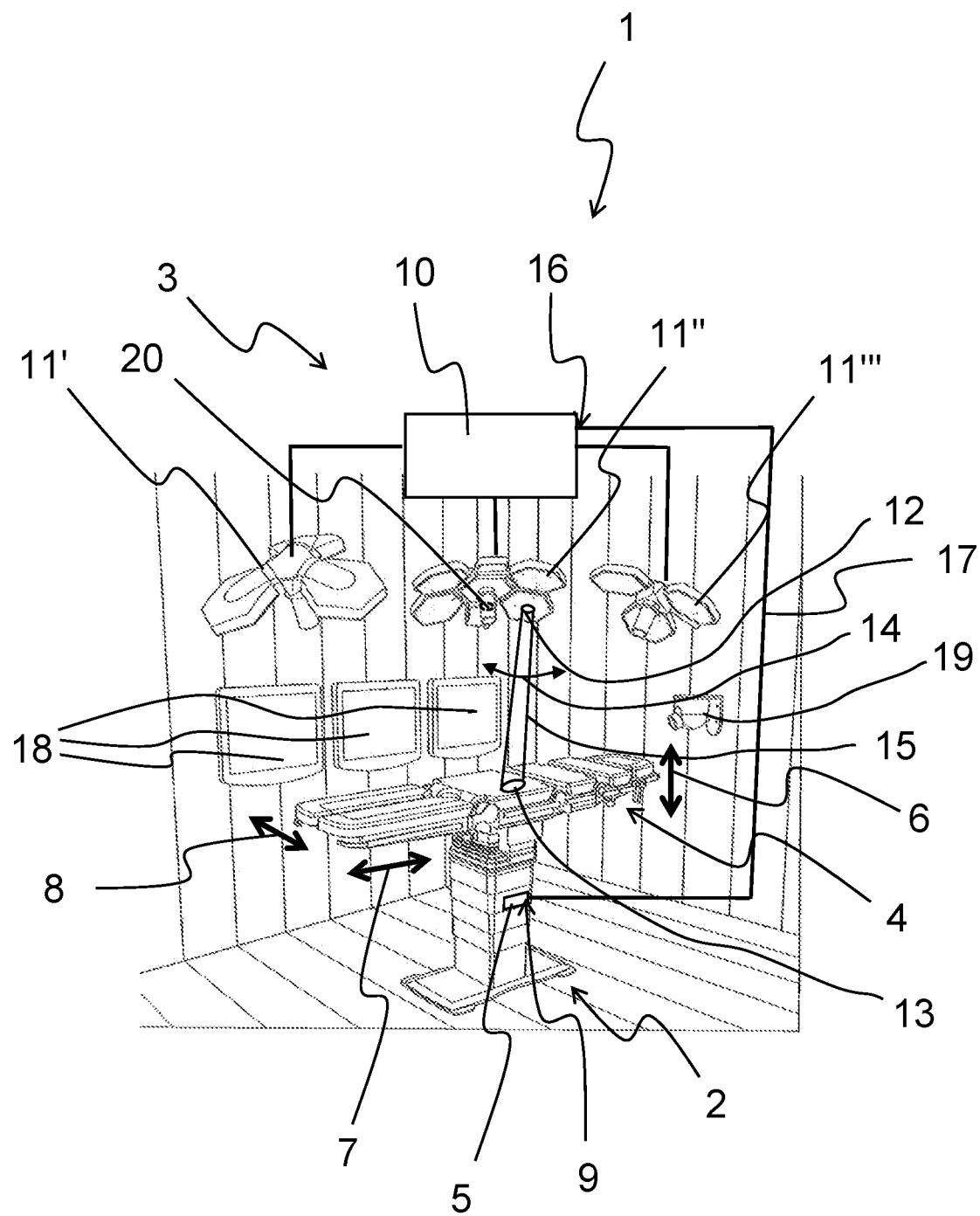

SURGICAL TABLE, SURGICAL LIGHT, SYSTEM COMPRISING SURGICAL TABLE AND SURGICAL LIGHT, AND METHOD FOR OPERATING THE SYSTEM

CROSS-REFERENCE TO RELATED APPLICATIONS

This application claims the benefit of European Patent Application Serial No. EP20177500.4, filed May 29, 2020, the entire disclosure of which is incorporated herein by reference in its entirety.

BACKGROUND

The disclosure relates to a surgical table, a surgical light, a system comprising a surgical table and surgical light, and a method for operating the system, wherein, in particular, the surgical table and the surgical light are provided with controllers for controlling functions of the surgical table and surgical light.

During surgical interventions, a posture of a patient is changed often during the procedure. Thereby, a position and a posture of a tabletop of an operating table has to be changed. For example, the tabletop has to be moved in a horizontal or a vertical direction, or it has to be tilted about a longitudinal or transversal axis. After such a repositioning of the patient, the illumination by a surgical light has to be adjusted which hinders the surgical intervention.

In the meantime, there are surgical lights which measure a distance between a lamp body of the surgical light and a surgical site for adjusting the illumination of the surgical site when the surgical light is moved; however, an adjustment based on only the distance is not sufficient in the case of if the tabletop performs another motion than a change in height. Thus, there is a need to further address the adjustment of the surgical lights based on the compound movement of the surgical table.

SUMMARY

The present disclosure includes one or more of the features recited in the appended claims and/or the following features which, alone or in any combination, may comprise patentable subject matter.

According to a first aspect of the disclosure, a surgical table comprises a surgical table controller configured to control at least one surgical table actuator of the surgical table, wherein the surgical table controller comprises a surgical table controller interface configured to be connectable to a controller of a further medical apparatus.

In some embodiments, the surgical table controller interface may be configured to be connectable to a controller of a further medical apparatus to provide the opportunity to exchange data or signals with the further medical apparatus in order to attune a respective behavior of the surgical table and the further medical apparatus. The controller of the further medical apparatus may control functions of the further medical apparatus based on an operator input from any user interface and/or based on sensor signals to the controller of the further medical apparatus.

According to a second aspect of the disclosure, a surgical light comprises a surgical light controller configured to turn on and off and to control an intensity of at least one illuminant of the surgical light, wherein the surgical light controller comprises a surgical light controller interface configured to be connectable to a controller of a further medical apparatus.

In some embodiments, the surgical light controller interface may be configured to be connectable to a controller of a further medical apparatus to provide the opportunity to exchange data or signals with the further medical apparatus in order to attune a respective behavior of the surgical light and the further medical apparatus. In particular, the surgical light may be turned on and off and the intensity of the illumination may be adjusted according to requests of the further medical apparatus. The controller of the further medical apparatus may control functions of the further medical apparatus based on an operator input from any user interface and/or based on sensor signals to the controller of the further medical apparatus.

In some embodiments, the surgical light may comprise at least one surgical light actuator controlled by the surgical light controller for changing a direction of emission of a light beam of at least one of the at least one illuminant. In such an embodiment, a location of an illuminated spot may be modified according to requests of the further medical apparatus.

According to a third aspect of the disclosure, a system comprises a surgical table and a surgical light is provided, wherein the surgical table controller and the surgical light controller are configured to be connected to one another. In such a system, the surgical table and the surgical light may exchange data for attuning their behaviors to one another. For example, upon provision of necessary sensors, the surgical table is enabled to perform motions according to a posture of the surgical light.

In some embodiments of the system, the surgical table controller interface and surgical light controller interface may comprise a communication path connecting the surgical table controller interface and surgical light controller interface via cable. In such an embodiment, the communication path via cable may have improved functioning and be without problems as far as possible. Such a communication is, for example, less sensitive concerning EMC and regulatory requirements can easier be fulfilled than in case of a use of a wireless communication.

In some embodiments of the system, the surgical table controller interface and surgical light controller interface may have a communication path connecting the surgical table controller interface and surgical light controller interface via wireless connection. Such a communication may be more comfortable in use since, without the use of cables, a risk of tripping over the cables is eliminated and, furthermore, establishing the communication can be facilitated since, compared to wired installation, efforts for installation are significantly reduced and, also, existing systems can be easily retrofitted.

According to a fourth aspect of the disclosure, a method includes the steps: actuating the at least one surgical table actuator by operating the surgical table controller, transmitting a signal relating to an actuation of the at least one surgical table actuator to the surgical light controller by the surgical table controller, and changing an illumination by the at least one illuminant by the surgical light controller according to the actuation of the surgical table actuator.

In some embodiments of the method, attuning a respective behavior of the surgical light and the surgical table may be possible. In particular, an illumination by the surgical light may be adjusted according to requests of the surgical table due to actuation of a specific surgical table actuator.

In some embodiments of the method, when receiving the signal relating to an actuation of the at least one surgical table actuator, the surgical light controller may initiate detection of a distance between a lamp body and a surgical site and may, thereby, change the illumination by the at least one illuminant according to the detected distance. By initiating the detection of the distance between the lamp body and the surgical site when receiving the signal relating to an actuation of the at least one surgical table actuator and changing the illumination according to the detected distance, unnecessary adjustments of the illumination, e.g., initiated by detecting temporarily present obstacles, may be avoided.

In some embodiments of the method, when receiving the signal relating to an actuation of the at least one surgical table actuator, the surgical light controller may initiate detection of at least one characteristic of the illumination of the surgical site and may change the illumination by the at least one illuminant according to the at least one detected characteristic. By initiating the detection of the characteristic of the illumination of the surgical site when receiving the signal relating to an actuation of the at least one surgical table actuator and changing the illumination according to the detected characteristic, unnecessary adjustments of the illumination, e.g., initiated by detecting temporarily present glaring obstacles changing the characteristic of the illumination, e.g., a light distribution, a shape, or a size of the surgical site, may be avoided. In some embodiments of the method, the at least one detected characteristic comprises a brightness of the surgical site. When detecting the brightness of the surgical site when receiving the signal relating to an actuation of the at least one surgical table actuator, the brightness as an important characteristic may be adapted according to a changed position of the tabletop performed by the at least one surgical table actuator.

In some embodiments of the method, the surgical light controller may change the illumination according to a type and value of the signal. In such embodiments, no detection of the distance between the lamp body and the surgical site or of the characteristic is necessary but the illumination may be adjusted directly to the changed position of the tabletop.

In some embodiments of the method, the changing of the illumination by the at least one illuminant may comprise changing of an intensity of the at least one illuminant. By the changing of the illumination, a brightness of a surgical site may be adjusted to actions of the surgical table.

In some embodiments of the method, the at least one surgical table actuator may change a height of a tabletop of the surgical table, and the intensity of the at least one illuminant may be increased upon reducing the height of the tabletop, and the intensity of the at least one illuminant may be decreased upon increasing the height of the tabletop. In such embodiments, a direct correlation between the actuation of a surgical table actuator initiating a height adjustment of the tabletop and the change of the intensity of the surgical light may be enabled. The change of the intensity of the at least one illuminant which may be adjusted according to a distance between a tabletop of the surgical table and a lamp body of the surgical light modified by the height adjustment of the tabletop enables a sufficient illumination of a surgical site in case of an enlargement of a distance between the lamp body of the surgical light and the surgical site and it enables avoiding of glaring of the surgical personnel in case of a reduction of the distance between the lamp body of the surgical light and the surgical site.

In some embodiments of the method, the method may include the further step: changing a direction of emission of a light beam of the at least one illuminant according to the actuation of the at least one surgical table actuator. In such embodiments, a direct correlation between the actuation of a surgical table actuator initiating a displacement of the tabletop and the change of the direction of emission of a light beam of the at least one illuminant may be enabled.

In some embodiments of the method, the at least one surgical table actuator may change a height of a tabletop of the surgical table, and the direction of a light beam of the at least one illuminant may be changed in order to illuminate an identical spot on the tabletop. In such embodiments, there may be a direct correlation between the actuation of a surgical table actuator initiating a height adjustment of the tabletop and the change of the direction of emission of a light beam of the at least one illuminant case, in particular, the surgical site may be illuminated by the illuminants from a position of the lamp body lateral from the surgical site and the height of the tabletop may be changed by the surgical table actuator, is enabled.

In some embodiments of the method, the at least one surgical table actuator may change a horizontal position of a tabletop of the surgical table, and the direction of a light beam of the at least one illuminant may be changed in order to illuminate an identical spot on the tabletop. In such an embodiment, a direct correlation between the actuation of a surgical table actuator initiating a horizontal displacement of the tabletop and the change of the direction of emission of a light beam of the at least one illuminant may be enabled.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying FIGURES in which:

FIG. 1 shows a system comprising a surgical table and a surgical light.

DETAILED DESCRIPTION

FIG. 1 shows a system 1 comprising a surgical table 2 and a surgical light 3. In FIG. 1, further medical apparatuses, such as monitors 18 and a camera 19 are illustrated.

The surgical table 2 comprises a tabletop 4, a surgical table controller 5 and surgical table actuators 6, 7, 8 for initiating specific functions of the surgical table 2. The surgical table actuator 6 is depicted by an up-down arrow for being illustrated as an actuator for changing a height of the tabletop 4. The surgical table actuator 7 is depicted by an arrow along a longitudinal direction of the tabletop for being illustrated as an actuator for a displacement of the tabletop 4 in a longitudinal direction thereof in order to change a horizontal position of the tabletop 4. The surgical table actuator 8 is depicted by an arrow along a transversal direction of the tabletop for being illustrated as an actuator for a displacement of the tabletop 4 in a transversal direction thereof in order to change a horizontal position of the tabletop 4. Moreover, the surgical table 2 comprises further surgical table actuators (not shown) as actuator for tilting the tabletop 4 around an axis in the transversal direction of the tabletop 4 and as actuator for tilting the tabletop 4 around an axis in the longitudinal direction. In alternative embodiments, the surgical table 2 does not comprise all of these actuators and/or comprises further actuators.

The surgical table controller 5 controls the surgical table actuators 6, 7, 8 in order to initiate motions of components of the surgical table 2. The surgical table controller 5 is provided with a surgical table controller interface 9 which is configured to be connectable to a controller of a further medical apparatus 3, 18, 19.

The controller of the further medical apparatus 3, 18, 19 is not provided as merely being a user interface but, actually, as a controller controlling functions of the further medical apparatus based on an operator input from any user interface and/or based on sensor signals to the controller of the further medical apparatus.

The surgical light 3 comprises a surgical light controller 10. The surgical light 3 is illustrated as comprising three lamp bodies 11', 11", 11''' joined to the surgical light controller 10; however, in alternative embodiments, another quantity of lamp bodies 11', 11", 11''' can be provided. In a further alternative embodiment, each of the lamp bodies 11', 11", 11''' is provided with an own surgical light controller 10, or several groups of lamp bodies 11', 11", 11''' are provided with a respective own surgical light controller 10.

The surgical light 3 comprises several illuminants 12, wherein only one of the several illuminants is illustrated and denominated with a reference sign. The illuminant 12 generates a light field in order to illuminate a spot 13 on the tabletop 4, in particular on the surgical site of a patient. Alternatively, the surgical light 3 comprises only one illuminant 12.

The surgical light 3 further comprises surgical light actuators 14. One of the surgical light actuators 14 is depicted by a bent arrow for being illustrated as a surgical light actuator for changing a direction of emission of a light beam 15 of the illuminant 12. Anyone of the illuminants 12 is provided with a surgical light actuator 14 for changing the direction of emission of its light beam 15. Alternatively, merely some of the illuminants 12 are respectively provided with one of the surgical light actuators 14. In a further alternative embodiment, none of the illuminants 12 is provided with a surgical light actuator 14. As the case may be, alternatively, the entire lamp body 11', 11", 11''' is provided with a surgical light actuator 14 for simultaneously changing the direction of emission of all of the light beams 15 of the illuminants 12 of the lamp body 11', 11", 11'''.

Moreover, the surgical light 3 comprises a distance detection unit 20. The distance detection unit 20 is configured to determine a distance between the lamp body 11', 11", 11''' and the surgical site. Signals of the distance detection unit 20 are transmitted to the surgical light controller 10. In alternative embodiments, the distance detection unit 20 is not provided but at least one other sensor detecting a characteristic of the illumination of the surgical site, e.g., a size or a color temperature, is provided, the at least one other sensor is provided additionally to the distance detection unit 20, or no sensor and distance detection unit are provided.

The surgical light controller 10 turns on and off and controls an intensity of the illuminants 12 of the surgical light 3. The surgical light controller 10 further controls the surgical light actuators 14 for changing the direction of emission of the light beam 15 of the illuminants 12. The surgical light controller 10 is provided with a surgical light controller interface 16 which is configured to be connectable to a controller of a further medical apparatus.

The surgical table controller 5 and the surgical light controller 10 are connected to one another and comprise a communication path 17. The communication path 17 is established via a wireless connection. The wireless connection comprises a WLAN connection. Alternatively, another wireless connection, such as a Bluetooth connection, or a wired communication path via cable is provided.

In use, when the surgical table controller 5 is actuated, for example, by a remote control (not shown), a respective surgical table actuator 6, 7, 8 is actuated by the surgical table controller 5. The surgical table controller 5 further transmits a signal relating to the actuation of the respective surgical table actuator 6, 7, 8 to the surgical light controller 10.

When the surgical light controller 10 receives the signal relating to the actuation of the surgical table actuator 6, 7, 8, the surgical light controller 10 initiates detection of a distance between the lamp body 11', 11", 11''' and the surgical site and changes the illumination by the illuminant 12 according to the detected distance. Alternatively, the surgical light controller 10 initiates detection of at least one characteristic of the illumination of the surgical site and changes the illumination by the illuminant 12 according to the at least one detected characteristic. The characteristic comprises a brightness of the surgical site or, additionally or alternatively, e.g., a size of the light field or a color temperature.

The surgical light controller 10 changes the illumination by the illuminants 12 according to the actuation of the surgical table actuator 6, 7, 8 by the surgical table controller 5 according to the detected distance and/or characteristic of the illumination or, additionally or alternatively, according to a type and value of the signal, e.g., a signal indicating a direction and an amount of a height adjustment of the tabletop 4. The change of the illumination comprises changing of the intensity of the illuminants 12. The change of the illumination comprises changing the direction of emission of the light beams 15 of the illuminants 12 according to the actuation of the surgical table actuator 6, 7, 8. In an alternative embodiment, no change of the direction of emission of the light beams 15 of the illuminants 12 according to the actuation of the surgical table actuator 6, 7, 8 is provided.

In case that the height of the tabletop 4 is changed by the surgical table actuator 6, the intensity of the illuminants 12 is increased upon reducing the height of the tabletop 4 and the intensity of the illuminants 12 is decreased upon enlarging the height of the tabletop 4.

Furthermore, in particular, in case that the surgical site is illuminated by the illuminants 12 from a position of the lamp body 11', 11", 11''' lateral from the surgical site and the height of the tabletop 4 is changed by the surgical table actuator 6, the direction of the light beams 15 of the illuminants 12 is changed in order to illuminate an identical spot 13 on the tabletop 4, in particular, on the surgical site of the patient.

Moreover, in case that the horizontal position of the tabletop 4 is changed by the surgical table actuator 7 or the surgical table actuator 8, the direction of the light beams 15 of the illuminants 12 is changed in order to illuminate the identical spot 13 on the tabletop 4, in particular, on the surgical site of the patient.

While the disclosure has been illustrated and described in detail in the drawing and the foregoing description, such illustration and description are to be considered illustrative or exemplary and not restrictive. The invention is not limited to the disclosed embodiments. From reading the present disclosure, other modifications will be apparent to a person skilled in the art. Such modifications may involve other features, which are already known in the art and may be used instead of or in addition to features already described herein.

In the claims, the word "comprising" does not exclude other elements or steps, and the indefinite article "a" or "an" does not exclude a plurality.

Although this disclosure refers to specific embodiments, it will be understood by those skilled in the art that various changes in form and detail may be made without departing from the subject matter set forth in the accompanying claims.

The invention claimed is:

1. A system comprising
a surgical table controller configured to control at least one surgical table actuator of the surgical table, wherein the surgical table controller comprises a surgical table controller interface configured to be connectable to a controller of a further medical apparatus, and
a surgical light controller configured to turn on and off and to control an intensity of at least one illuminant of the surgical light, wherein the surgical light controller comprises a surgical light controller interface configured to be connectable to a controller of a further medical apparatus,
wherein the surgical table controller and the surgical light controller are configured to be connected to one another such that an illumination of the at least one illuminant of the surgical light by the surgical light controller is changed based on the actuation of the at least one surgical table actuator.

2. The system of claim 1, wherein the surgical table controller interface and surgical light controller interface comprise a communication path connecting the surgical table controller interface and surgical light controller interface via a cable.

3. The system of claim 2, wherein the surgical table controller interface and surgical light controller interface comprise a communication path connecting the surgical table controller interface and surgical light controller interface via a wireless connection.

4. A system comprising
a surgical table controller configured to control at least one surgical table actuator of the surgical table, wherein the surgical table controller comprises a surgical table controller interface configured to be connectable to a controller of a further medical apparatus, and
a surgical light controller configured to turn on and off and to control an intensity of at least one illuminant of the surgical light, wherein the surgical light controller comprises a surgical light controller interface configured to be connectable to a controller of a further medical apparatus,
wherein the surgical table controller and the surgical light controller are configured to be connected to one another, and wherein when receiving a signal relating to an actuation of the at least one surgical table actuator, the surgical light controller initiates detection of a distance between a lamp body and a surgical site and changes the illumination by the at least one illuminant according to the detected distance.

5. A system comprising
a surgical table controller configured to control at least one surgical table actuator of the surgical table, wherein the surgical table controller comprises a surgical table controller interface configured to be connectable to a controller of a further medical apparatus, and
a surgical light controller configured to turn on and off and to control an intensity of at least one illuminant of the surgical light, wherein the surgical light controller comprises a surgical light controller interface configured to be connectable to a controller of a further medical apparatus,
wherein the surgical table controller and the surgical light controller are configured to be connected to one another, and
wherein when receiving the signal relating to an actuation of the at least one surgical table actuator, the surgical light controller initiates detection of at least one characteristic of the illumination of the surgical site and changes the illumination by the at least one illuminant according to the at least one detected characteristic.

6. The system of claim 5, wherein the at least one detected characteristic comprises a brightness of the surgical site.

7. The system of claim 1, wherein the surgical light controller changes the illumination according to a type and value of a signal.

8. The system of claim 1, wherein the changing of the illumination by the at least one illuminant comprises changing of an intensity of the at least one illuminant.

9. The system of claim 1, wherein the at least one surgical table actuator changes a height of a tabletop of the surgical table, and the intensity of the at least one illuminant is increased upon reducing the height of the tabletop, and the intensity of the at least one illuminant is decreased upon increasing the height of the tabletop.

10. A system comprising
a surgical table controller configured to control at least one surgical table actuator of the surgical table, wherein the surgical table controller comprises a surgical table controller interface configured to be connectable to a controller of a further medical apparatus, and
a surgical light controller configured to turn on and off and to control an intensity of at least one illuminant of the surgical light, wherein the surgical light controller comprises a surgical light controller interface configured to be connectable to a controller of a further medical apparatus,
wherein the surgical table controller and the surgical light controller are configured to be connected to one another, and
wherein the surgical light controller changes a direction of emission of a light beam of the at least one illuminant according to the actuation of the at least one surgical table actuator and when the at least one surgical table actuator changes a height of a tabletop of the surgical table, the direction of the light beam of the at least one illuminant is changed in order to illuminate an identical spot on the tabletop.

11. The system of claim 10, wherein when the at least one surgical table actuator changes a horizontal position of a tabletop of the surgical table the direction of a light beam of the at least one illuminant is changed in order to illuminate an identical spot on the tabletop.

12. A method for operating a system including a surgical table having a controller and a surgical light having a controller, the surgical table controller in communication with the surgical light controller, the method including the steps:
actuating at least one surgical table actuator by operating the surgical table controller;
transmitting a signal relating to an actuation of the at least one surgical table actuator to the surgical light controller by the surgical table controller; and
changing an illumination of at least one illuminant of the surgical light by the surgical light controller based on the actuation of the at least one surgical table actuator.

13. The method of claim 12, wherein when receiving the signal relating to an actuation of the at least one surgical table actuator, the surgical light controller initiates detection of a distance between a lamp body and a surgical site and changes the illumination by the at least one illuminant according to the detected distance.

14. The method of claim 12, wherein when receiving the signal relating to an actuation of the at least one surgical table actuator, the surgical light controller initiates detection of at least one characteristic of the illumination of the surgical site and changes the illumination by the at least one illuminant according to the at least one detected characteristic.

15. The method of claim 14, wherein the at least one detected characteristic comprises a brightness of the surgical site.

16. The method of claim 12, wherein the surgical light controller changes the illumination according to a type and value of the signal.

17. The method of claim 12, wherein the changing of the illumination by the at least one illuminant comprises changing of an intensity of the at least one illuminant.

18. The method of claim 17, wherein the at least one surgical table actuator changes a height of a tabletop of the surgical table, and the intensity of the at least one illuminant is increased upon reducing the height of the tabletop, and the intensity of the at least one illuminant is decreased upon enlarging the height of the tabletop.

19. The method of claim 12 including the further step:
   changing a direction of emission of a light beam of the at least one illuminant according to the actuation of the at least one surgical table actuator.

20. The method of claim 19, wherein the at least one surgical table actuator changes a height of a tabletop of the surgical table, and the direction of the light beam of the at least one illuminant is changed in order to illuminate an identical spot on the tabletop.

21. The method of claim 19, wherein the at least one surgical table actuator changes a horizontal position of a tabletop of the surgical table, and the direction of a light beam of the at least one illuminant is changed in order to illuminate an identical spot on the tabletop.

* * * * *